US007267121B2

(12) United States Patent
Ivri

(10) Patent No.: US 7,267,121 B2
(45) Date of Patent: *Sep. 11, 2007

(54) AEROSOL DELIVERY APPARATUS AND METHOD FOR PRESSURE-ASSISTED BREATHING SYSTEMS

(75) Inventor: Ehud Ivri, Newport Beach, CA (US)

(73) Assignee: Aerogen, Inc., Mountain View, CA (US)

( * ) Notice: Subject to any disclaimer, the term of this patent is extended or adjusted under 35 U.S.C. 154(b) by 106 days.

This patent is subject to a terminal disclaimer.

(21) Appl. No.: 10/957,321

(22) Filed: Sep. 30, 2004

(65) Prior Publication Data

US 2005/0229929 A1     Oct. 20, 2005

Related U.S. Application Data

(63) Continuation-in-part of application No. 10/883,115, filed on Jun. 30, 2004, which is a continuation-in-part of application No. 10/828,765, filed on Apr. 20, 2004.

(51) Int. Cl.
*A61M 15/00* (2006.01)
*A61M 16/10* (2006.01)
*A61M 16/00* (2006.01)
*A61M 11/00* (2006.01)
*H05B 3/00* (2006.01)

(52) U.S. Cl. .......................... 128/203.17; 128/203.16; 128/203.22; 128/203.24; 128/200.14; 128/200.21

(58) Field of Classification Search ........... 128/200.16, 128/203.12, 204.18, 204.23, 200.14, 200.21, 128/203.16, 203.17, 203.22, 203.24, 204.14
See application file for complete search history.

(56) References Cited

U.S. PATENT DOCUMENTS 550,315 A     11/1895     Allen (Continued)

FOREIGN PATENT DOCUMENTS

CH     477 885     9/1969

(Continued)

OTHER PUBLICATIONS

Abys, J.A. et al., "Annealing Behavior of Palladium-Nickel Alloy Electrodeposits," Plating and Surface Finishing, Aug. 1996, pp. 1-7.

(Continued)

*Primary Examiner*—Justine R. Yu
*Assistant Examiner*—Kristen Matter
(74) *Attorney, Agent, or Firm*—Townsend and Townsend and Crew LLP

(57) ABSTRACT

A pressure-assisted breathing system is provided that comprises: a pressure-generating circuit for maintaining a positive pressure within the system; a patient interface device coupled to a patient's respiratory system; a respiratory circuit for providing gas communication between the pressure-generating circuit and the patient interface device; means for introducing aerosol particles into the gas flow in the respiratory circuit; and means for discontinuing the introduction of aerosol particles into said respiratory circuit gas flow when the patient exhales. In one embodiment, a flow sensor is disposed in an auxiliary circuit in fluid communication with the respiratory circuit and electronically coupled with a nebulizer. The flow sensor is adapted to detect changes in the volumetric flow rate of gas in the auxiliary circuit when the patient exhales and stops exhaling and sends corresponding electronic signals to the nebulizer to turn off and turn on, respectively.

13 Claims, 3 Drawing Sheets

U.S. PATENT DOCUMENTS

| | | | |
|---|---|---|---|
| 809,159 A | 1/1906 | Willis et al. | |
| 1,680,616 A | 8/1928 | Horst | |
| 2,022,520 A | 11/1935 | Philbrick | |
| 2,101,304 A | 12/1937 | Wright | |
| 2,158,615 A | 5/1939 | Wright | |
| 2,187,528 A | 1/1940 | Wing | |
| 2,223,541 A | 12/1940 | Baker | |
| 2,266,706 A | 12/1941 | Fox et al. | |
| 2,283,333 A | 5/1942 | Martin | |
| 2,292,381 A | 8/1942 | Klagges | |
| 2,360,297 A | 10/1944 | Wing | |
| 2,375,770 A | 5/1945 | Dahlberg | |
| 2,383,098 A | 8/1945 | Wheaton | |
| 2,404,063 A | 7/1946 | Healy | |
| 2,430,023 A | 11/1947 | Longmaid | |
| 2,474,996 A | 7/1949 | Wallis | |
| 2,512,004 A | 6/1950 | Wing | |
| 2,521,657 A | 9/1950 | Severy | |
| 2,681,041 A | 6/1954 | Zodtner et al. | |
| 2,705,007 A | 3/1955 | Gerber | |
| 2,735,427 A | 2/1956 | Sullivan | |
| 2,764,946 A | 10/1956 | Henderson | |
| 2,764,979 A | 10/1956 | Henderson | |
| 2,779,623 A | 1/1957 | Eisenkraft | |
| 2,935,970 A | 5/1960 | Morse et al. | |
| 3,103,310 A | 9/1963 | Lang | |
| 3,325,031 A | 6/1967 | Singler | |
| 3,411,854 A | 11/1968 | Rosler et al. | |
| 3,515,348 A | 6/1970 | Coffman, Jr. | |
| 3,550,864 A | 12/1970 | East | |
| 3,558,052 A | 1/1971 | Dunn | |
| 3,561,444 A | 2/1971 | Boucher | |
| 3,563,415 A | 2/1971 | Ogle | |
| 3,680,954 A | 8/1972 | Frank | |
| 3,719,328 A | 3/1973 | Hindman | |
| 3,738,574 A | 6/1973 | Guntersdorfer et al. | |
| 3,771,982 A | 11/1973 | Dobo | |
| 3,790,079 A | 2/1974 | Berglund et al. | |
| 3,804,329 A | 4/1974 | Martner | |
| 3,812,854 A * | 5/1974 | Michaels et al. | 128/200.16 |
| 3,838,686 A | 10/1974 | Szekely | |
| 3,842,833 A | 10/1974 | Ogle | |
| 3,865,106 A | 2/1975 | Palush | |
| 3,903,884 A | 9/1975 | Huston et al. | |
| 3,906,950 A | 9/1975 | Cocozza | |
| 3,908,654 A | 9/1975 | Lhoest et al. | |
| 3,950,760 A | 4/1976 | Rauch et al. | |
| 3,951,313 A | 4/1976 | Coniglione | |
| 3,958,249 A | 5/1976 | DeMaine et al. | |
| 3,970,250 A | 7/1976 | Drews | |
| 3,983,740 A | 10/1976 | Danel | |
| 3,993,223 A | 11/1976 | Welker, III et al. | |
| 4,005,435 A | 1/1977 | Lundquist et al. | |
| 4,020,834 A | 5/1977 | Bird | |
| 4,030,492 A | 6/1977 | Simburner | |
| 4,052,986 A | 10/1977 | Scaife | |
| 4,059,384 A | 11/1977 | Holland et al. | |
| D246,574 S | 12/1977 | Meierhoefer | |
| 4,076,021 A | 2/1978 | Thompson | |
| 4,083,368 A | 4/1978 | Freezer | |
| 4,094,317 A | 6/1978 | Wasnich | |
| 4,101,041 A | 7/1978 | Mauro, Jr. et al. | |
| 4,106,503 A | 8/1978 | Rosenthal et al. | |
| 4,109,174 A | 8/1978 | Hodgson | |
| 4,113,809 A | 9/1978 | Abair et al. | |
| D249,958 S | 10/1978 | Meierhoefer | |
| 4,119,096 A | 10/1978 | Drews | |
| 4,121,583 A | 10/1978 | Chen | |
| 4,159,803 A | 7/1979 | Cameto et al. | |
| 4,207,990 A | 6/1980 | Weiler et al. | |
| 4,210,155 A | 7/1980 | Grimes | |
| 4,226,236 A | 10/1980 | Genese | |
| 4,240,081 A | 12/1980 | Devitt | |
| 4,240,417 A | 12/1980 | Holever | |
| 4,248,227 A | 2/1981 | Thomas | |
| 4,261,512 A | 4/1981 | Zierenberg | |
| D259,213 S | 5/1981 | Pagels | |
| 4,268,460 A | 5/1981 | Boiarski et al. | |
| 4,294,407 A | 10/1981 | Reichl et al. | |
| 4,298,045 A | 11/1981 | Weiler et al. | |
| 4,299,784 A | 11/1981 | Hense | |
| 4,300,546 A | 11/1981 | Kruber | |
| 4,301,093 A | 11/1981 | Eck | |
| 4,301,810 A * | 11/1981 | Belman | 600/533 |
| 4,319,155 A | 3/1982 | Makai et al. | |
| 4,334,531 A | 6/1982 | Reichl et al. | |
| 4,336,544 A | 6/1982 | Donald et al. | |
| 4,338,576 A | 7/1982 | Takahashi et al. | |
| 4,340,044 A * | 7/1982 | Levy et al. | 128/204.21 |
| 4,368,476 A | 1/1983 | Uehara et al. | |
| 4,368,850 A | 1/1983 | Szekely | |
| 4,374,707 A | 2/1983 | Pollack | |
| 4,389,071 A | 6/1983 | Johnson, Jr. et al. | |
| 4,408,719 A | 10/1983 | Last | |
| 4,428,802 A | 1/1984 | Kanai et al. | |
| 4,431,136 A | 2/1984 | Janner et al. | |
| 4,454,877 A | 6/1984 | Miller et al. | |
| 4,465,234 A | 8/1984 | Maehara et al. | |
| 4,474,251 A | 10/1984 | Johnson, Jr. | |
| 4,474,326 A | 10/1984 | Takahashi | |
| 4,475,113 A | 10/1984 | Lee et al. | |
| 4,479,609 A | 10/1984 | Maeda et al. | |
| 4,484,577 A * | 11/1984 | Sackner et al. | 128/203.28 |
| 4,502,481 A * | 3/1985 | Christian | 128/205.24 |
| 4,512,341 A | 4/1985 | Lester | |
| 4,530,464 A | 7/1985 | Yamamoto et al. | |
| 4,533,082 A | 8/1985 | Maehara et al. | |
| 4,539,575 A | 9/1985 | Nilsson | |
| 4,544,933 A | 10/1985 | Heinzl | |
| 4,546,361 A | 10/1985 | Brescia et al. | |
| 4,550,325 A | 10/1985 | Viola | |
| 4,566,452 A | 1/1986 | Farr | |
| 4,591,883 A | 5/1986 | Isayama | |
| 4,593,291 A | 6/1986 | Howkins | |
| 4,605,167 A | 8/1986 | Maehara | |
| 4,613,326 A | 9/1986 | Szwarc | |
| 4,620,201 A | 10/1986 | Heinzl et al. | |
| 4,628,890 A | 12/1986 | Freeman | |
| 4,632,311 A | 12/1986 | Nakane et al. | |
| 4,658,269 A | 4/1987 | Rezanka | |
| 4,659,014 A | 4/1987 | Soth et al. | |
| 4,677,975 A | 7/1987 | Edgar et al. | |
| 4,678,680 A | 7/1987 | Abowitz | |
| 4,679,551 A | 7/1987 | Anthony | |
| 4,681,264 A | 7/1987 | Johnson, Jr. | |
| 4,693,853 A | 9/1987 | Falb et al. | |
| 4,702,418 A | 10/1987 | Carter et al. | |
| 4,722,906 A | 2/1988 | Guire | |
| 4,753,579 A | 6/1988 | Murphy | |
| 4,790,479 A | 12/1988 | Matsumoto et al. | |
| 4,793,339 A | 12/1988 | Matsumoto et al. | |
| 4,796,807 A | 1/1989 | Bendig et al. | |
| 4,799,622 A | 1/1989 | Ishikawa et al. | |
| 4,805,609 A | 2/1989 | Roberts et al. | |
| 4,819,629 A | 4/1989 | Jonson | |
| 4,819,834 A | 4/1989 | Thiel | |
| 4,826,080 A | 5/1989 | Ganser | |
| 4,826,759 A | 5/1989 | Guire et al. | |
| 4,828,886 A | 5/1989 | Hieber | |
| 4,843,445 A | 6/1989 | Stemme | |
| 4,849,303 A | 7/1989 | Graham et al. | |
| 4,850,534 A | 7/1989 | Takahashi et al. | |
| 4,852,563 A * | 8/1989 | Gross | 128/202.27 |
| 4,865,006 A | 9/1989 | Nogi et al. | |

| | | | | | | |
|---|---|---|---|---|---|---|
| 4,871,489 A | 10/1989 | Ketcham | | 5,320,603 A | 6/1994 | Vetter et al. |
| 4,872,553 A | 10/1989 | Suzuki et al. | | 5,322,057 A | 6/1994 | Raabe et al. |
| 4,877,989 A | 10/1989 | Drews et al. | | 5,342,011 A | 8/1994 | Short |
| 4,888,516 A | 12/1989 | Daeges et al. | | 5,342,504 A | 8/1994 | Hirano et al. |
| 4,922,901 A | 5/1990 | Brooks et al. | | 5,347,998 A | 9/1994 | Hodson et al. |
| 4,926,915 A | 5/1990 | Deussen et al. | | 5,348,189 A | 9/1994 | Cater |
| 4,934,358 A | 6/1990 | Nilsson et al. | | 5,350,116 A | 9/1994 | Cater |
| 4,951,661 A * | 8/1990 | Sladek .................. 128/202.27 | | 5,355,872 A | 10/1994 | Riggs et al. |
| 4,954,225 A | 9/1990 | Bakewell | | 5,357,946 A | 10/1994 | Kee et al. |
| 4,957,239 A | 9/1990 | Tempelman | | 5,372,126 A | 12/1994 | Blau |
| 4,964,521 A | 10/1990 | Wieland et al. | | 5,383,906 A | 1/1995 | Burchett et al. |
| D312,209 S | 11/1990 | Morrow et al. | | 5,388,571 A | 2/1995 | Roberts et al. |
| 4,968,299 A | 11/1990 | Ahlstrand et al. | | 5,392,768 A | 2/1995 | Johansson et al. |
| 4,971,665 A | 11/1990 | Sexton | | 5,396,883 A | 3/1995 | Knupp et al. |
| 4,973,493 A | 11/1990 | Guire | | 5,414,075 A | 5/1995 | Swan et al. |
| 4,976,259 A | 12/1990 | Higson et al. | | 5,415,161 A | 5/1995 | Ryder |
| 4,979,959 A | 12/1990 | Guire | | 5,419,315 A | 5/1995 | Rubsamen |
| 4,994,043 A | 2/1991 | Ysebaert | | 5,426,458 A | 6/1995 | Wenzel et al. |
| 5,002,048 A | 3/1991 | Makiej, Jr. | | 5,431,155 A | 7/1995 | Marelli |
| 5,002,582 A | 3/1991 | Guire et al. | | 5,435,282 A | 7/1995 | Haber et al. |
| 5,007,419 A | 4/1991 | Weinstein et al. | | 5,435,297 A | 7/1995 | Klein |
| 5,016,024 A | 5/1991 | Lam et al. | | 5,437,267 A | 8/1995 | Weinstein et al. |
| 5,021,701 A | 6/1991 | Takahashi et al. | | 5,445,141 A | 8/1995 | Kee et al. |
| 5,022,587 A | 6/1991 | Hochstein | | D362,390 S | 9/1995 | Weiler |
| 5,024,733 A | 6/1991 | Abys et al. | | 5,449,502 A | 9/1995 | Igusa et al. |
| 5,046,627 A | 9/1991 | Hansen | | 5,452,711 A | 9/1995 | Gault |
| 5,062,419 A | 11/1991 | Rider | | 5,458,135 A | 10/1995 | Patton et al. |
| 5,063,396 A | 11/1991 | Shiokawa et al. | | 5,458,289 A | 10/1995 | Cater |
| 5,063,922 A * | 11/1991 | Hakkinen .............. 128/200.16 | | 5,474,059 A | 12/1995 | Cooper |
| 5,073,484 A | 12/1991 | Swanson et al. | | 5,477,992 A | 12/1995 | Jinks et al. |
| 5,076,266 A | 12/1991 | Babaev | | 5,479,920 A | 1/1996 | Piper et al. |
| 5,080,093 A | 1/1992 | Raabe et al. | | 5,485,850 A | 1/1996 | Dietz |
| 5,080,649 A | 1/1992 | Vetter | | 5,487,378 A | 1/1996 | Robertson et al. |
| 5,086,765 A | 2/1992 | Levine | | 5,489,266 A | 2/1996 | Grimard |
| 5,086,785 A | 2/1992 | Gentile et al. | | 5,497,944 A | 3/1996 | Weston et al. |
| 5,115,803 A | 5/1992 | Sioutas | | D369,212 S | 4/1996 | Snell |
| 5,115,971 A | 5/1992 | Greenspan et al. | | 5,511,726 A | 4/1996 | Greenspan et al. |
| D327,008 S | 6/1992 | Friedman | | 5,512,329 A | 4/1996 | Guire et al. |
| 5,122,116 A | 6/1992 | Kriesel et al. | | 5,512,474 A | 4/1996 | Clapper et al. |
| 5,129,579 A | 7/1992 | Conte | | 5,515,841 A | 5/1996 | Robertson et al. |
| 5,134,993 A | 8/1992 | Van Der Linden et al. | | 5,515,842 A | 5/1996 | Ramseyer et al. |
| 5,139,016 A | 8/1992 | Waser | | 5,516,043 A | 5/1996 | Manna et al. |
| 5,140,740 A | 8/1992 | Weigelt | | 5,518,179 A | 5/1996 | Humberstone et al. |
| 5,147,073 A | 9/1992 | Cater | | 5,529,055 A | 6/1996 | Gueret |
| 5,152,456 A | 10/1992 | Ross et al. | | 5,533,497 A | 7/1996 | Ryder |
| 5,157,372 A | 10/1992 | Langford | | 5,537,997 A * | 7/1996 | Mechlenburg et al. .. 128/204.23 |
| 5,164,740 A | 11/1992 | Ivri | | 5,542,410 A | 8/1996 | Goodman et al. |
| 5,169,029 A | 12/1992 | Behar et al. | | 5,549,102 A | 8/1996 | Lintl et al. |
| 5,170,782 A | 12/1992 | Kocinski | | 5,560,837 A | 10/1996 | Trueba |
| 5,180,482 A | 1/1993 | Abys et al. | | 5,563,056 A | 10/1996 | Swan et al. |
| 5,186,164 A | 2/1993 | Raghuprasad | | D375,352 S | 11/1996 | Bologna |
| 5,186,166 A | 2/1993 | Riggs et al. | | 5,570,682 A * | 11/1996 | Johnson .................. 128/200.14 |
| 5,198,157 A | 3/1993 | Bechet | | 5,579,757 A | 12/1996 | McMahon et al. |
| 5,201,322 A | 4/1993 | Henry et al. | | 5,582,330 A | 12/1996 | Iba |
| 5,207,623 A * | 5/1993 | Tkatchouk et al. ........... 482/61 | | 5,584,285 A * | 12/1996 | Salter et al. ............ 128/200.21 |
| 5,213,860 A | 5/1993 | Laing | | 5,586,550 A | 12/1996 | Ivri et al. |
| 5,217,148 A | 6/1993 | Cater | | 5,588,166 A | 12/1996 | Burnett |
| 5,217,492 A | 6/1993 | Guire et al. | | 5,601,077 A | 2/1997 | Imbert |
| 5,227,168 A | 7/1993 | Chvapil | | 5,609,798 A | 3/1997 | Liu et al. |
| 5,230,496 A | 7/1993 | Shillington et al. | | 5,632,878 A | 5/1997 | Kitano |
| 5,245,995 A | 9/1993 | Sullivan et al. | | 5,635,096 A | 6/1997 | Singer et al. |
| 5,248,087 A | 9/1993 | Dressler | | 5,637,460 A | 6/1997 | Swan et al. |
| 5,258,041 A | 11/1993 | Guire et al. | | 5,647,349 A | 7/1997 | Ohki et al. |
| 5,261,601 A | 11/1993 | Ross et al. | | 5,653,227 A | 8/1997 | Barnes et al. |
| 5,263,992 A | 11/1993 | Guire | | 5,654,007 A | 8/1997 | Johnson et al. |
| 5,279,568 A | 1/1994 | Cater | | 5,654,162 A | 8/1997 | Guire et al. |
| 5,297,734 A | 3/1994 | Toda | | 5,654,460 A | 8/1997 | Rong |
| 5,299,739 A | 4/1994 | Takahashi et al. | | 5,657,926 A | 8/1997 | Toda |
| 5,303,854 A | 4/1994 | Cater | | 5,660,166 A | 8/1997 | Lloyd |
| 5,309,135 A | 5/1994 | Langford | | 5,664,557 A | 9/1997 | Makiej, Jr. |
| 5,312,281 A | 5/1994 | Takahashi et al. | | 5,664,706 A | 9/1997 | Cater |
| 5,313,955 A | 5/1994 | Rodder | | 5,665,068 A | 9/1997 | Takamura |
| 5,319,971 A | 6/1994 | Osswald et al. | | 5,666,946 A | 9/1997 | Langenback |

| | | | | | | |
|---|---|---|---|---|---|---|
| 5,670,999 A | 9/1997 | Takeuchi et al. | | 6,158,431 A | 12/2000 | Poole |
| 5,685,491 A | 11/1997 | Marks et al. | | 6,161,536 A | 12/2000 | Redmon et al. |
| 5,692,644 A | 12/1997 | Gueret | | 6,163,588 A | 12/2000 | Matsumoto et al. |
| 5,694,923 A * | 12/1997 | Hete et al. ............. 128/204.18 | | 6,182,662 B1 | 2/2001 | McGhee |
| 5,707,818 A | 1/1998 | Chudzik et al. | | 6,186,141 B1 | 2/2001 | Pike et al. |
| 5,709,202 A | 1/1998 | Lloyd et al. | | 6,196,218 B1 | 3/2001 | Voges |
| 5,714,360 A | 2/1998 | Swan et al. | | 6,196,219 B1 | 3/2001 | Hess et al. |
| 5,714,551 A | 2/1998 | Bezwada et al. | | 6,205,999 B1 | 3/2001 | Ivri et al. |
| 5,718,222 A | 2/1998 | Lloyd et al. | | 6,216,916 B1 | 4/2001 | Maddox et al. |
| D392,184 S | 3/1998 | Weiler | | 6,223,746 B1 | 5/2001 | Jewett et al. |
| 5,724,957 A | 3/1998 | Rubsamen et al. | | 6,235,177 B1 | 5/2001 | Borland et al. |
| 5,744,515 A | 4/1998 | Clapper | | 6,254,219 B1 | 7/2001 | Agarwal et al. |
| 5,752,502 A | 5/1998 | King | | 6,269,810 B1 * | 8/2001 | Brooker et al. ........ 128/203.12 |
| 5,755,218 A | 5/1998 | Johansson et al. | | 6,270,473 B1 | 8/2001 | Schwebel |
| 5,758,637 A | 6/1998 | Ivri et al. | | 6,273,342 B1 | 8/2001 | Terada et al. |
| 5,775,506 A | 7/1998 | Grabenkort | | 6,318,640 B1 | 11/2001 | Coffee |
| 5,788,665 A | 8/1998 | Sekins | | 6,328,030 B1 | 12/2001 | Kidwell et al. |
| 5,788,819 A | 8/1998 | Onishi et al. | | 6,328,033 B1 | 12/2001 | Avrahami |
| 5,790,151 A | 8/1998 | Mills | | 6,341,732 B1 | 1/2002 | Martin et al. |
| 5,810,004 A | 9/1998 | Ohki et al. | | 6,358,058 B1 | 3/2002 | Strupat et al. |
| 5,819,730 A | 10/1998 | Stone et al. | | 6,394,363 B1 | 5/2002 | Arnott et al. |
| 5,823,179 A | 10/1998 | Grychowski et al. | | 6,402,046 B1 | 6/2002 | Loser |
| 5,823,428 A | 10/1998 | Humberstone et al. | | 6,405,934 B1 | 6/2002 | Hess et al. |
| 5,829,723 A | 11/1998 | Brunner et al. | | 6,427,682 B1 | 8/2002 | Klimowicz et al. |
| 5,836,515 A | 11/1998 | Fonzes | | 6,443,146 B1 | 9/2002 | Voges |
| 5,839,617 A | 11/1998 | Cater et al. | | 6,443,366 B1 | 9/2002 | Hirota et al. |
| 5,842,468 A | 12/1998 | Denyer et al. | | 6,467,476 B1 | 10/2002 | Ivri et al. |
| 5,862,802 A | 1/1999 | Bird | | 6,467,477 B1 * | 10/2002 | Frank et al. ............ 128/203.23 |
| 5,865,171 A | 2/1999 | Cinquin | | 6,530,370 B1 | 3/2003 | Heinonen |
| 5,878,900 A | 3/1999 | Hansen | | 6,540,153 B1 | 4/2003 | Ivri |
| 5,893,515 A | 4/1999 | Hahn et al. | | 6,540,154 B1 | 4/2003 | Ivri et al. |
| 5,894,841 A | 4/1999 | Voges | | 6,543,443 B1 | 4/2003 | Klimowicz et al. |
| 5,897,008 A | 4/1999 | Hansen | | 6,546,927 B2 | 4/2003 | Litherland et al. |
| 5,910,698 A | 6/1999 | Yagi | | 6,550,472 B2 | 4/2003 | Litherland et al. |
| 5,915,377 A | 6/1999 | Coffee | | 6,554,201 B2 | 4/2003 | Klimowicz et al. |
| 5,918,637 A | 7/1999 | Fleischman | | 6,581,595 B1 | 6/2003 | Murdock et al. |
| 5,925,019 A | 7/1999 | Ljungquist | | 6,615,824 B2 | 9/2003 | Power |
| 5,938,117 A | 8/1999 | Ivri | | 6,629,646 B1 | 10/2003 | Ivri |
| 5,950,619 A | 9/1999 | Van Der Linden et al. | | 6,640,804 B2 | 11/2003 | Ivri |
| 5,954,268 A | 9/1999 | Joshi et al. | | 6,651,650 B1 | 11/2003 | Yamamoto et al. |
| 5,960,792 A | 10/1999 | Lloyd et al. | | 6,688,304 B2 | 2/2004 | Gonda et al. |
| 5,964,417 A | 10/1999 | Amann et al. | | 6,705,315 B2 | 3/2004 | Sullivan et al. |
| 5,970,974 A | 10/1999 | Van Der Linden et al. | | 6,705,316 B2 * | 3/2004 | Blythe et al. .......... 128/204.18 |
| 5,976,344 A | 11/1999 | Abys et al. | | 6,725,858 B2 * | 4/2004 | Loescher ................ 128/200.14 |
| 5,993,805 A | 11/1999 | Sutton et al. | | 6,732,944 B2 | 5/2004 | Litherland et al. |
| 6,000,396 A | 12/1999 | Melker et al. | | 6,745,768 B2 | 6/2004 | Colla et al. |
| 6,007,518 A | 12/1999 | Kriesel et al. | | 6,745,770 B2 | 6/2004 | McAuliffe et al. |
| 6,012,450 A | 1/2000 | Rubsamen | | 6,755,189 B2 | 6/2004 | Ivri et al. |
| 6,014,970 A | 1/2000 | Ivri et al. | | 6,769,626 B1 | 8/2004 | Haveri |
| 6,026,809 A | 2/2000 | Abrams et al. | | 6,782,886 B2 | 8/2004 | Narayan et al. |
| 6,029,666 A | 2/2000 | Aloy et al. | | 6,805,118 B2 * | 10/2004 | Brooker et al. ........ 128/203.12 |
| 6,032,665 A | 3/2000 | Psaros | | 6,810,876 B2 | 11/2004 | Berthon-Jones |
| 6,037,587 A | 3/2000 | Dowell et al. | | 6,814,071 B2 | 11/2004 | Klimowicz et al. |
| 6,039,696 A | 3/2000 | Bell | | 6,817,361 B2 | 11/2004 | Berthon-Jones et al. |
| 6,045,215 A | 4/2000 | Coulman | | 6,840,240 B1 | 1/2005 | Berthon-Jones et al. |
| 6,045,874 A | 4/2000 | Himes | | 6,845,770 B2 | 1/2005 | Klimowicz et al. |
| 6,047,818 A | 4/2000 | Warby et al. | | 6,851,626 B2 | 2/2005 | Patel et al. |
| 6,055,869 A | 5/2000 | Stemme et al. | | 6,860,268 B2 * | 3/2005 | Bohn et al. ............. 128/206.21 |
| 6,060,128 A | 5/2000 | Kim et al. | | 6,904,906 B2 * | 6/2005 | Salter et al. ........... 128/200.21 |
| 6,062,212 A | 5/2000 | Davison et al. | | 7,152,597 B2 * | 12/2006 | Bathe .................... 128/202.27 |
| 6,068,148 A | 5/2000 | Weiler | | 2001/0013554 A1 | 8/2001 | Borland et al. |
| 6,085,740 A | 7/2000 | Ivri et al. | | 2001/0015737 A1 | 8/2001 | Truninger et al. |
| 6,096,011 A | 8/2000 | Trombley, III et al. | | 2002/0011247 A1 | 1/2002 | Ivri et al. |
| 6,105,877 A | 8/2000 | Coffee | | 2002/0023650 A1 | 2/2002 | Gunaratnam et al. |
| 6,106,504 A | 8/2000 | Urrutia | | 2002/0033178 A1 | 3/2002 | Farrell et al. |
| 6,116,234 A | 9/2000 | Genova et al. | | 2002/0036601 A1 | 3/2002 | Puckeridge et al. |
| 6,123,413 A | 9/2000 | Agarwal et al. | | 2002/0078958 A1 | 6/2002 | Stenzler |
| 6,139,674 A | 10/2000 | Markham et al. | | 2002/0104530 A1 | 8/2002 | Ivri et al. |
| 6,142,146 A | 11/2000 | Abrams et al. | | 2002/0121274 A1 | 9/2002 | Borland et al. |
| 6,145,963 A | 11/2000 | Pidwerbecki et al. | | 2002/0134372 A1 | 9/2002 | Loeffler et al. |
| 6,146,915 A | 11/2000 | Pidwerbecki et al. | | 2002/0134374 A1 | 9/2002 | Loeffler et al. |
| 6,152,130 A | 11/2000 | Abrams et al. | | 2002/0134375 A1 | 9/2002 | Loeffler et al. |
| 6,155,676 A | 12/2000 | Etheridge et al. | | 2002/0134377 A1 | 9/2002 | Loeffler et al. |

| | | |
|---|---|---|
| 2002/0162551 A1 | 11/2002 | Litherland |
| 2002/0195107 A1 | 12/2002 | Smaldone |
| 2003/0140921 A1 | 7/2003 | Smith et al. |
| 2003/0145859 A1 | 8/2003 | Bohn et al. |
| 2003/0150445 A1 | 8/2003 | Power et al. |
| 2003/0150446 A1 | 8/2003 | Patel et al. |
| 2003/0226906 A1 | 12/2003 | Ivri |
| 2004/0000598 A1 | 1/2004 | Ivri |
| 2004/0004133 A1 | 1/2004 | Ivri et al. |
| 2004/0011358 A1 | 1/2004 | Smaldone et al. |
| 2004/0035413 A1 | 2/2004 | Smaldone et al. |
| 2004/0035490 A1 | 2/2004 | Power |
| 2004/0050947 A1 | 3/2004 | Power et al. |
| 2004/0139963 A1 | 7/2004 | Ivri et al. |
| 2004/0139968 A1 | 7/2004 | Loeffler et al. |
| 2004/0188534 A1 | 9/2004 | Litherland et al. |
| 2004/0194783 A1 | 10/2004 | McAuliffe et al. |
| 2004/0226561 A1 | 11/2004 | Colla et al. |
| 2004/0226566 A1 | 11/2004 | Gunaratnam et al. |
| 2004/0256488 A1 | 12/2004 | Loeffler et al. |
| 2005/0011514 A1 | 1/2005 | Power et al. |
| 2005/0039746 A1 | 2/2005 | Grychowski et al. |
| 2005/0139211 A1 | 6/2005 | Alston et al. |
| 2005/0150496 A1 | 7/2005 | Smaldone |
| 2005/0211245 A1 | 9/2005 | Smaldone et al. |
| 2005/0211253 A1 | 9/2005 | Smaldone et al. |
| 2005/0220763 A1 | 10/2005 | Condos et al. |
| 2005/0235987 A1 | 10/2005 | Smaldone et al. |
| 2005/0284469 A1 | 12/2005 | Tobia et al. |

FOREIGN PATENT DOCUMENTS

| | | |
|---|---|---|
| CH | 555 681 | 11/1974 |
| DE | 11 03 522 | 3/1961 |
| DE | 3513628 C1 * | 10/1986 |
| EP | 0 049 636 A1 | 4/1982 |
| EP | 0 103 161 A2 | 3/1984 |
| EP | 0 134 847 A1 | 3/1985 |
| EP | 0 178 925 A2 | 4/1986 |
| EP | 0 387 222 A1 | 9/1990 |
| EP | 0 432 992 A1 | 6/1991 |
| EP | 0 476 991 B1 | 3/1992 |
| EP | 0 480 615 A1 | 4/1992 |
| EP | 0 510 648 A2 | 10/1992 |
| EP | 0 516 565 A1 | 12/1992 |
| EP | 0 542 723 A2 | 5/1993 |
| EP | 0 933 138 A2 | 4/1999 |
| EP | 0 923 957 A1 | 6/1999 |
| EP | 1 142 600 A1 | 10/2001 |
| EP | 2865801 * | 8/2005 |
| GB | 973 458 | 10/1964 |
| GB | 1 454 597 | 11/1976 |
| GB | 2 073 616 A | 10/1981 |
| GB | 2 101 500 | 1/1983 |
| GB | 2 177 623 A | 1/1987 |
| GB | 2 240 494 A | 7/1991 |
| GB | 2 272 389 A | 5/1994 |
| JP | 57-023852 | 2/1982 |
| JP | 57-105608 | 7/1982 |
| JP | 58-061857 | 4/1983 |
| JP | 58-139757 | 8/1983 |
| JP | 59-142163 A | 8/1984 |
| JP | 60-004714 | 1/1985 |
| JP | 61-008357 A | 1/1986 |
| JP | 61-215059 A | 9/1986 |
| JP | 02-135169 | 5/1990 |
| JP | 02-189161 | 7/1990 |
| JP | 60-07721 A | 1/1994 |
| SU | 490474 * | 3/1976 |
| WO | WO82/03548 A | 10/1982 |
| WO | WO92/07600 A1 | 5/1992 |
| WO | WO92/11050 A1 | 9/1992 |
| WO | WO92/17231 A1 | 10/1992 |
| WO | WO93/01404 A1 | 1/1993 |
| WO | WO93/10910 A1 | 6/1993 |
| WO | WO94/09912 A1 | 5/1994 |
| WO | WO96/09229 | 3/1996 |
| WO | WO99/17888 | 4/1999 |
| WO | WO 00/37132 | 6/2000 |

OTHER PUBLICATIONS

Allen, T. *Particle Size Measurement*, Third Edition, Chapman and Hall pp. 167-169 (1981).

Ashgriz, N. et al. "Development of a Controlled Spray Generator" Rev. Sci. Instrum., 1987, pp. 1291-1296, vol. 58, No. 7.

Berglund, R.N., et al. "Generation of Monodisperse Aerosol Standards" Environ. Sci. Technology, Feb. 1973, pp. 147-153, vol. 7, No. 2.

Cipolla, D.C. et al., "Assessment of Aerosol Delivery Systems for Recombinant Human Deoxyribonuclease," S.T.P. Pharma Sciences 4 (1) 50-62, 1994.

Cipolla, D.C. et al., "Characterization of Aerosols of Human Recombinant Deoxyribonuclease I (rhDNase) Generated by Neulizers," Pharmaceutical Research II (4) 491-498, 1994.

Dogan, Aydin PhD, Thesis: "Flexional 'Moonie and Cymbal' Actuators", Penn State University, 1994.

Fink, James B. et al. "Aerosol Drug Therapy," Clinical Practice in Respiratory Care; Chapter 12, pp. 308-342; 1999.

Gaiser Tool Company catalog, pp. 26, 29-30 (1990).

Gonda, I. "Therapeutic Aerosols," Pharmaceutics, The Science of Dosage Form Design, Editor: M.E. Aulton, 341-358, 1988.

Hancock, B.C. et al., "Molecular Mobility of Amorphous Pharmaceutical Solids Below Their Glass Transition Temperatures," Pharmaceutical Research 12, 799-806 (1995).

Heyder, J. et al., "Deposition of particles in the human respiratory tract in the size range 0.005-15 microns." J Aerosol Sci 17: 811-825, 1986.

Hickey, Anthony J. "Pharmaceutical Inhalation Aerosol Technology," Drugs And The Pharmaceutical Science, 1992, pp. 172-173, vol. 54.

Hikayama, H., et al. "Ultrasonic Atomizer with Pump Function" Tech. Rpt. IEICE Japan US88-74:25 (1988).

Maehara, N. et al. "Atomizing rate control of multi-pinhole-plate ultrasonic atomizer" J. Acoustical Soc. Japan, 1988, pp. 116-121, 44:2.

Maehara, N. et al. "Influence of the vibrating system of a multipinhole-plate ultrasonic nebulizer on its performance" Review of Scientific Instruments, Nov. 1986, p. 2870-2876, vol. 57, No. 1.

Maehara, N. et al. "Influences of liquid's physical properties on the characteristics of a multi-pinhole-plate ultrasonic atomizer" J. Acoustical Soc. Japan 1988, pp. 425-431, 44:6.

Maehara, N. et al. "Optimum Design Procedure for Multi-Pinhole-Plate Ultrasonic Atomizer" Japanese Journal of Applied Physics, 1987, pp. 215-217, vol. 26, Supplement 26-1.

Nogi, T. et al. "Mixture Formation of Fuel Injection System in Gasoline Engine" Nippon Kikai Gakkai Zenkoku Taikai Koenkai Koen Ronbunshu 69:660-662 (1991).

Palla Tech Pd an Pd Alloy Processes—Procedure for the Analysis of Additive IVS in Palla Tech Plating Solutions by HPLC, Technical Bulletin, Electroplating Chemicals & Services, 029-A, Lucent Technologies,, pp. 1-5, 1996.

Siemens, "Servo Ultra Nebulizer 345 Operating Manual," pp. 1-23.

TSI Incorporated product catalog. Vibrating Orifice Aerosol Generator (1989).

Ueha, S., et al. "Mechanism of Ultrasonic Atomization Using a Multi-Pinhole Plate" J. Acoust. Soc. Jpn., 1985, pp. 21-26, (E)6,1.

Wehl, Wolfgang R. "Ink-Jet Printing: The Present State of the Art" for Siemans AG, 1989.

Berggren, E. "Pilot Study of Nebulized Surfactant Therapy for Neonatal Respiratory Distress Syndrome", Acta Paediatr 89: 460-464, Taylor & Francis, ISSN 0803-5253, 2000, Sweden.

Duarte, Alexander G. et al. "Inhalation Therapy During Mechanical Ventialation" Respiratory Care Clinics of North America, Aerosol Therapy, Jun. 2001, pp. 233-259, vol. 7, No. 2.

Fink, James B. et al. "Aerosol Therapy in Mechanically Ventilated Patients: Recent Advances and New Techniques" Seminars in Respiratory and Critical Care Medicine, 2000, pp. 183-201, vol. 21, No. 3.

Fink, James B. et al. Diagram from and abstract of article entitled "Optimizing efficiency of nebulizers during mechanical ventilation: The effect of placement and type of ventilator circuit" Chest, Oct. 1999, 116:312S.

Jorch, G. Letter to the Editor, "Surfactant Aerosol Treatment of Respiratory Distress Syndrome in Spontaneously Breathing Premature Infants", Pediatric Pulmonology 24: 222-224, 1997, Wiley-Liss, Inc.

Smaldone, G. C. "Aerosolized Antibiotics: Current and Future", Respiratory Care, vol. 45, No. 6, pp. 667-675.

Smedsaas-Löfvenbert, A. "Nebulization of Drugs in a Nasal CPAP System", Scandinavian University Press, 1999, Acta Paediatr 88: 89-92, Sweden.

\* cited by examiner

AEROSOL DELIVERY APPARATUS AND METHOD FOR PRESSURE-ASSISTED BREATHING SYSTEMS

CROSS-REFERENCES TO RELATED APPLICATIONS

This application is a continuation-in-part of U.S. application Ser. No. 10/828,765, filed Apr. 20, 2004, and is related to U.S. application Ser. No. 10/883,115, filed Jun. 30, 2004, both of which are incorporated by reference herein in their entirety.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

This invention relates to apparatus and methods for delivering medication to the respiratory system of a patient, preferably an infant, through a pressure-assisted breathing system. More specifically, one aspect of the invention is directed to apparatus and methods for coupling a flow sensor with a continuous positive airway pressure ("CPAP") system that employs a nebulizer, preferably one having a vibrating aperture-type aerosol generator, to deliver aerosolized medicament simultaneously with CPAP treatment.

The use of CPAP systems and therapies are conventional forms of ventilation treatment for respiratory disorders in both adults and children. In particular, it has been reported that respiratory support with nasal CPAP ("NCPAP"), coupled with simultaneous treatment with nebulized drugs, preferably surfactants, has several advantages in the treatment of infant respiratory distress syndrome ("iRDS") in pre-term infants ("neonates"). For example, early application of NCPAP and early treatment with aerosolized surfactant in neonates with iRDS have been found to be effective in decreasing the need for mechanical ventilation, with its accompanying mechanical and infectious risks and pathophysiological effects. See, for example, "To the Editor: Surfactant Aerosol Treatment of Respiratory Distress Syndrome in Spontaneously Breathing Premature Infants"; *Pediatric Pulmonology* 24:22-224 (1997); "Early Use of Surfactant, NCPAP Improves Outcomes in Infant Respiratory Distress Syndrome"; *Pediatrics* 2004; 11;e560-e563 (as reported online by Medscape Medical News group, Jun. 4, 2004); and "Nebulization of Drugs in a Nasal CPAP System"; Acta Pediatric 88: 89-92 (1999).

CPAP systems utilize a constant positive pressure during inhalation to increase and maintain lung volumes and to decrease the work by a patient during spontaneous breathing. The positive pressure effectively dilates the airway and prevents its collapse. The delivery of positive airway pressure is accomplished through the use of a positive air flow source ("flow generator") that provides oxygen or a gas containing oxygen through a flexible tube connected to a patient interface device such as nasal prongs (cannula), nasopharyngeal tubes or prongs, an endotracheal tube, mask, etc. CPAP systems typically maintain and control continuous positive airway pressure by using a restrictive air outlet device, e.g. a fixed orifice or threshold resistor, or a pressure valve, which modulates the amount of gas leaving the circuit to which the patient interface device is attached. This pressure regulating device may be placed at, before or beyond the patient interface device and defines a primary pressure-generating circuit.

During the course of conventional CPAP therapy, the patient may typically inhale only a fraction of the total flow of gas passing through the primary pressure-generating circuit. For example, it has been estimated that a CPAP gas flow of 8 L/min may typically result in a pharyngeal tube flow of about 2/L min. As a result, only 25% of aerosolized medicament introduced into the CPAP flow will enter the pharynx. In addition, from this 25% entering the pharynx, about two-thirds may be lost during expiration, assuming an inspiratory/expiratory ratio of 1:2. Thus, in conventional CPAP systems, only 10% of the nebulized drug may enter the patient interface device. This waste, particularly with extremely expensive surfactants, makes the cost of administering nebulized drugs through conventional CPAP systems unacceptably high for routine clinical use. To reduce these costs, the prior art has identified the need for improvements in the method of delivery for aerosolized drugs, e.g. it has been suggested that a method and apparatus are needed for restricting nebulization to inspiration only. See, for example, the article in Pediatric Pulmonology, supra.

It is therefore desirable to find ways to decrease the losses of aerosol particles within pressure-assisted breathing systems during the exhalation phase of the respiratory cycle. In particular, increasing the efficiency in the delivery of aerosolized medicaments through CPAP systems, and the resulting smaller amounts of medicament required for a treatment, can represent a substantial advantage, particularly when scarce and expensive medicaments are employed.

BRIEF SUMMARY OF THE INVENTION

The present invention provides a pressure-assisted breathing system, e.g. a CPAP system, comprising in one embodiment a pressure-generating circuit for maintaining a positive pressure within the system, a patient interface device coupled to a patient's respiratory system, a respiratory circuit for providing gas communication between the pressure-generating circuit and the patient interface device, means for introducing aerosol particles, e.g. an aerosolized medicament, into the gas flow in the respiratory circuit and means for discontinuing the introduction of aerosol particles into the respiratory circuit when the patient exhales.

In one embodiment of the invention, the means for discontinuing the introduction of aerosol particles comprises a flow sensor disposed in an auxiliary circuit in fluid communication with the respiratory circuit and electronically coupled with the means for introducing the aerosol particles into the respiratory circuit flow. A small portion of the gas flow in the respiratory circuit is diverted through the flow sensor by the auxiliary circuit. Preferably the flow rate in the auxiliary circuit is adjusted to be commensurate with the middle of the flow rate range detected by the flow sensor. Preferred flow sensors are adapted to detect small changes in the volumetric flow rate of gas in the auxiliary circuit and send a corresponding electronic signal to the means for introducing aerosol particles into the respiratory circuit.

In one embodiment of the invention, the means for introducing aerosol particles comprises a nebulizer, most preferably, a nebulizer having a reservoir for holding a liquid medicament to be delivered to the patient's respiratory system, a vibrating aperture-type aerosol generator for aerosolizing the liquid medicament and a connector for connecting the nebulizer to the respiratory circuit so as to entrain the aerosolized medicament from the aerosol generator into the gas flowing through the respiratory circuit. As previously mentioned, the nebulizer is preferably electronically coupled to the flow sensor through the electronic circuitry of the CPAP system.

As with conventional CPAP operation, a constant flow of gas is maintained in the respiratory circuit by the CPAP system of the present invention during inhalation by the patient (hereinafter referred to as "inspiratory flow"). In the practice of the present invention, a flow corresponding to the inspiratory flow, but at a lesser flow rate, is diverted to the auxiliary circuit. An adjustable valve, e.g. an orifice valve, is preferably provided in the auxiliary circuit to regulate the flow of gas through the flow sensor. This valve may be used to reduce the flow of gas in the respiratory circuit to a range that can be measured by the flow sensor, and preferably in the middle of this range. Particularly preferred flow sensors have a flow range of from 0 to 1 liter/minute ("L/min").

When the patient exhales, the flow of gas in the respiratory circuit (and correspondingly in the auxiliary circuit) increases as a result of the additional flow of gas generated by the patient's lungs (hereinafter referred to as "expiratory flow"). In a preferred embodiment, the flow sensor detects the change in the flow rate of gas in the auxiliary circuit corresponding to the expiratory flow in the respiratory circuit, and sends an electronic signal to turn off the aerosol generator of the nebulizer. When the expiratory flow ceases, the flow sensor detects the decrease in flow rate in the auxiliary circuit and discontinues the electronic signal to the nebulizer. As a result, the nebulizer turns on and resumes the introduction of aerosol particles into the respiratory circuit. In this way, the system of the present invention stops the delivery of aerosol particles during exhalation by the patient so that aerosol particles are introduced into the respiratory circuit only when the patient inhales.

A disposable filter is preferably positioned in the auxiliary circuit up-stream to the flow sensor. Since a portion of the expiratory flow is diverted into the auxiliary circuit, bacterial, viral or other contaminants emanating from the diseased patient's respiratory system may be present in the auxiliary circuit flow. The filter removes these contaminants before the air flow passes through the flow sensor and is preferably replaced with every new patient using the apparatus. This feature allows the flow sensor to be permanently connected to the electronic circuitry of the CPAP system and remain in place without contamination when the apparatus is used by different patients.

The present invention also provides a method of respiratory therapy wherein an aerosolized medicament is introduced into a pressure-assisted breathing system only when the patient inhales. In another embodiment, the invention provides a method of delivering an aerosol to a patient's respiratory system which comprises the steps of: (a) providing a pressure-assisted breathing system having a respiratory circuit wherein a constant inspiratory flow is provided to a patient during inhalation and an additional expiratory flow is generated by the patient during exhalation, (b) providing an auxiliary circuit to divert a portion of the total flow in the respiratory circuit to a flow sensor; (c) measuring the flow rate in the auxiliary circuit with the flow sensor when the total flow in the respiratory circuit comprises only the inspiratory flow, thereby producing a first electronic signal; (d) measuring the flow rate in the auxiliary circuit with the flow sensor when the total flow in the respiratory circuit comprises the sum of the inspiratory flow and the expiratory flow, thereby producing a second electronic signal; (e) providing a nebulizer electronically coupled to the flow sensor and adapted to introduce aerosol particles of medicament into the respiratory circuit when the first electronic signal is detected, and to stop the introduction of aerosol particles of medicament into the respiratory circuit when the second electronic signal is detected.

DETAILED DESCRIPTION OF THE INVENTION

Figure 1:
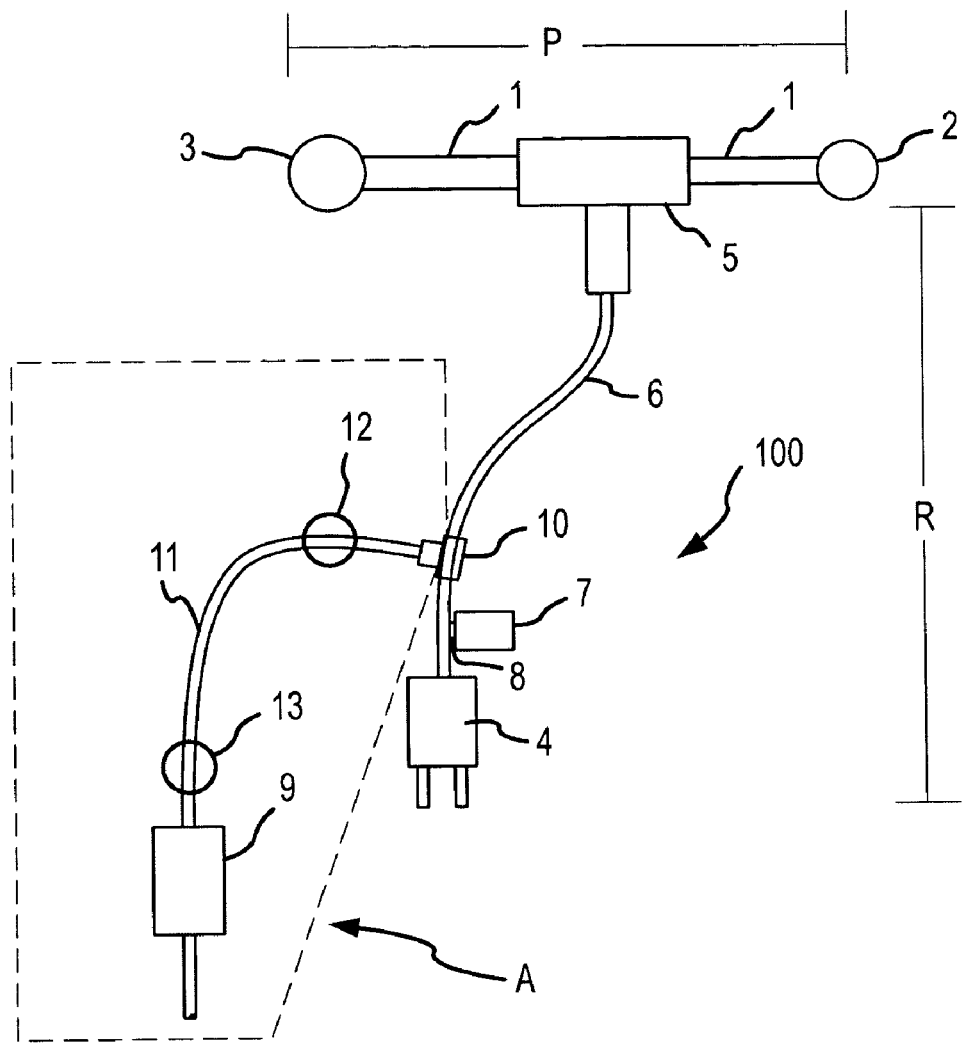
FIG. 1 is a schematic illustration of a CPAP system according to the present invention.

As shown in FIG. 1, one preferred embodiment of the invention comprises a CPAP system 100 having a primary pressure-generating circuit P, a respiratory circuit R and an auxiliary circuit A. The tubes associated with commercially available pressure-assisted breathing systems create a "circuit" for gas flow by maintaining fluid communication between the elements of the circuit. Tubes can be made of a variety of materials, including but not limited to various plastics, metals and composites and can be rigid or flexible. Tubes can be attached to various elements of the circuit in a detachable mode or a fixed mode using a variety of connectors, adapters, junction devices, etc. Circuit P includes a flow generator 2 in fluid communication through conduit 1 with a pressure-regulating device 3. One element is in "fluid communication" with another element when it is attached through a channel, port, tube or other conduit that permits the passage of gas, vapor and the like.

Respiratory circuit R includes a patient interface device, namely nasal cannula 4, which communicates with circuit P at "T"-shaped junction unit 5 through tube 6. Tube 6 is preferably a flexible tube having a smaller diameter than conduit 1, e.g. tube 6 may have an outside diameter of 5-8 mm or less. This arrangement allows the patient to move his/her head freely without disconnecting the patient interface device from the patient. Nebulizer 7 (comprising an aerosol generator) is in fluid communication with tube 6 at junction 8. Nebulizer 7 is adapted to emit an aerosolized medicament directly into the gas flow that is inhaled by the patient, i.e. the gas flow in respiratory circuit R, and is preferably located in the direct vicinity of the patient's nose, mouth or artificial airway (e.g. an endotracheal tube). Nebulizer 7 itself may comprise a built-in connector for connecting to tube 6 (as shown), or may be connected using a separate tube or connector.

Auxiliary circuit A includes flexible tube 11, preferably having the same outside diameter as tube 6, which connects flow sensor 9 with tube 6 at "T"-shaped junction unit 10. Junction unit 10 is preferably positioned close to nasal cannula 4, but upstream to nebulizer 7 so that aerosol particles emitted by nebulizer 7 are not diverted into tube 11. Adjustable orifice valve 12 may be positioned in tube 11 between junction 10 and flow sensor 9 to adjust the flow rate of gas passing through flow sensor 9, preferably to the middle of the optimal flow range for sensor 9. Disposable filter 13 may be positioned in tube 11 between junction 10 and flow sensor 9 to remove any bacterial, viral and/or other contaminants from the patient's diseased respiratory system that may be carried by the exhaled air passing through flow sensor 9.

Figure 2:
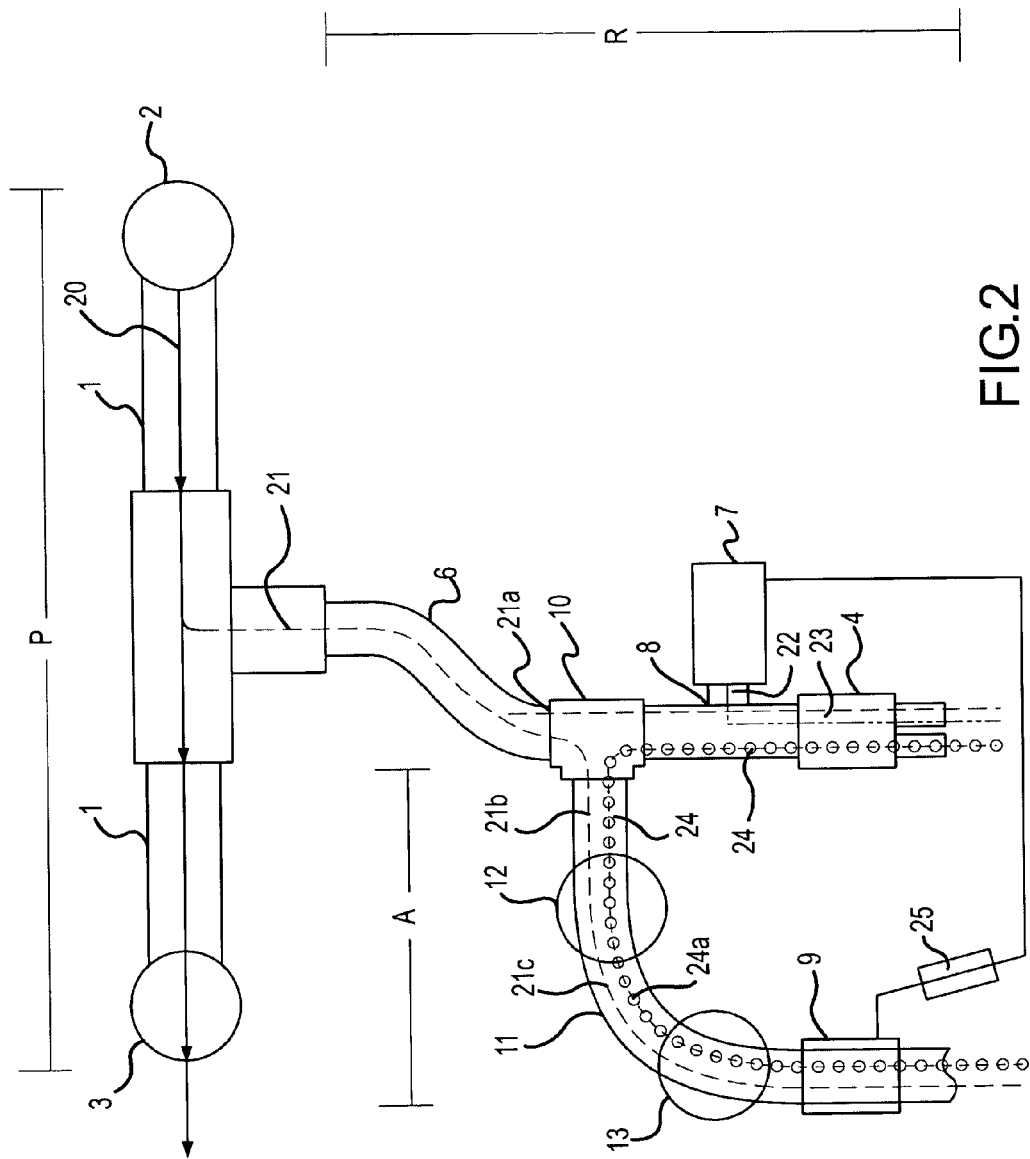
FIG. 2 is a cross-sectional view of the CPAP system of FIG. 1.

The operation of CPAP system 100 will be illustrated by referring to FIG. 2, which is an enlarged, cross-section view of CPAP system 100. A high volume flow of gas 20 is introduced into circuit P from flow generator 2 and passes through conduit 1 to pressure-regulating device 3 which maintains a continuous positive pressure throughout the system. Inspiratory flow 21, which may typically be about 10% of flow 20, flows from conduit 1 of pressure-generating circuit P into tube 6 of respiratory circuit R to provide a relatively constant inspiratory flow rate of air to the patient's respiratory system, thereby assisting in the patient's inspiratory efforts in accordance with conventional CPAP system principles. At junction 10, a portion 21a of inspiratory flow 21 proceeds through tube 6 to nasal cannula 4, and a portion 21b of inspiratory flow 21 is diverted through tube 11 to flow sensor 9.

Flow 21a passes through junction 8, at which point aerosolized medicament particles 22 produced by the aerosol generator of nebulizer 7 are introduced into flow 21a. Resulting flow 23 containing entrained aerosol particles 22 ultimately passes into the patient's respiratory system through nasal cannula 4, thereby delivering the aerosolized medicament to the patient's respiratory system. Flow 21b passes through tube 11 and adjustable orifice valve 12, which may be adjusted to reduce the rate of flow 21b to a reduced flow 21c, e.g. a flow rate that may be about 20% of the flow rate of flow 21b. Reduced flow 21c then proceeds through disposable filter 13 to flow sensor 9, and is ultimately released to the atmosphere. As flow 21c passes through flow sensor 9, flow sensor 9 measures the volumetric flow rate of flow 21c and generates a first electronic signal, e.g. a certain output voltage, in electronic circuitry 25 of CPAP system 100 that is characteristic of flow 21c. Since flow 21c is directly proportional to inspiratory flow 21, the first electronic signal caused by flow 21c may be used by the system to identify when the patient is inhaling and continue the delivery of aerosolized medicament.

When the patient exhales, expiratory flow 24 passes through nasal cannula 4 to tube 6 and is diverted through tube 11 at junction unit 10. Expiratory flow 24 is combined with inspiratory flow 21b in tube 11 to produce a flow rate equal to the sum of the flow rates of flow 24 and 21b. The combination of flow 24 and flow 21b passes through adjustable orifice valve 12 and the total flow rate is reduced in the same manner as previously described for flow 21b alone (identified in FIG. 2 as a combination of flow 21c and 24a). Disposable filter 13 removes any bacterial, viral or other contaminants that may have been present in the combined air flow as a result of flow 24a and the combined air flow then passes through flow sensor 9. When the combination of flow 21c and 24a passes through flow sensor 9, the change (increase) in flow rate over that of flow 21c alone is detected by flow sensor 9. As a result, flow sensor 9 generates a second electronic signal in electronic circuitry 25 that is different than the first electronic signal produced by flow 21c alone. The second electronic signal is transmitted by electronic circuitry 25 to nebulizer 7 and causes it to turn off its aerosol generator. This inactivation of the aerosol generator stops the introduction of aerosol particles 22 into flow 21a. Since the second electronic signal is generated by the volumetric flow rate of the combination of flow 21c and 24a, it indicates the presence of expiratory flow 24. Therefore, the second electronic signal may be used by the system to identify when the patient is exhaling and stop the introduction of aerosolized medicament. In this way, no aerosol is introduced into tube 6 when the patient exhales, and therefore, no aerosolized medicament is entrained in expiratory flow 24, which is ultimately released to the atmosphere and lost.

When expiratory effort by the patient stops and inhalation commences again, expiratory flow 24 discontinues and only inspiratory flow 21 is present in the system. As a result, only flow 21c passes through tube 11. Flow sensor 9 detects this change (decrease) in flow rate and generates the first electronic signal, which is transmitted to nebulizer 7. The first electronic signal causes nebulizer 7 to turn on the aerosol generator and resume the introduction of aerosol particles 22 into flow 21a. The turning on and off of the aerosol generator of nebulizer 7 in concert with the patient's respiratory cycle allows aerosolized medicament to be introduced into the CPAP system of the present invention only when the patient is inhaling. This results in a dramatic increase in the efficiency of delivery of the medicament and a corresponding reduction in losses of medicament to the atmosphere.

Flow generator 2 may conveniently comprise any of the known sources of pressurized gas suitable for use with pressure-assisted breathing systems such as CPAP systems. Typically, the flow generator is capable of supplying a flow of high-volume gas, which includes at least some portion of oxygen, at slightly greater than atmospheric pressure. For example, the source of pressurized gas may be an air blower or a ventilator, or the pressurized gas may originate from a wall supply of air and/or oxygen, such as that found within hospitals and medical facilities, or may originate from a pressurized cylinder or cylinders. The pressurized gas may comprise various known mixtures of oxygen with air, nitrogen, or other gases and may be provided in a single stream or flow to circuit R, for example, as shown by element 20 of FIG. 2.

Pressure-regulating device 3 may comprise any of the known devices for controlling and maintaining air pressure within a CPAP system at the desired constant level. Typically, pressure-regulating device 3 may comprise a restrictive air outlet device such as a pressure valve or threshold resistor that modulates the flow of gas leaving the pressure-regulating circuit P. In other applications, the modulation of the gas flow may be provided by releasing the air flow into a standardized vessel containing a predetermined quantity of water, with the pressure in the system being expressed in terms of the height to which the water rises in the vessel. Regardless of the pressure-regulating device used, the resistance to air flow in the pressure-generating circuit may be varied so that the continuous positive airway pressure conducted by respiratory circuit R to patient interface device 4 will suit the needs of the particular patient using the apparatus.

Although junction unit 5 may typically comprise a "T" or "Y"-shaped hollow unit (sometimes referred to as the "WYE"), it may take other shapes. As shown in FIG. 1, flexible tube 6 is connected to junction unit 5 and defines a branch gas conduit that depends from and is in gas communication with pressure-generating circuit P. Tube 6 is ultimately connected to a patient interface device, e.g. nasal cannula 4, to form respiratory circuit R. Flexible tube 6 is preferably relatively thin, smaller in diameter and more flexible than conduit 1 comprising pressure-generating circuit P. For example, flexible tube 6 may be commercially available silicone tubing having an outside diameter of about 5-8 mm.

The patient interface device 4 of the present invention may include any of the known devices for providing gas communication between the CPAP device and the patient's respiratory system. By way of example, the patient interface device may include nasal cannula or prongs (as shown in the Figures), an oral/nasal mask, a nasal mask, nasopharyngeal prongs, an endotracheal tube, a tracheotomy tube, a nasopharyngeal tube, and the like.

Nebulizer 7 may be any of the known devices for nebulizing (aerosolizing) drugs that are suitable for use with a CPAP system. Particularly preferred for the practice of this invention are those nebulizers having a vibrating aperture-type aerosol generator, for example, those nebulizers described in the present application's parent application and in U.S. Pat. Nos. 6,615,824; 5,164,740; 5,586,550; 5,758,637; and 6,085,740, and in copending U.S. patent application Ser. No. 10/465,023, filed Jun. 18, 2003, and Ser. No. 10/284,068, filed Oct. 30, 2002. The entire disclosures of said patents and applications are incorporated by reference herein. Particularly preferred nebulizers for the present invention are small and light-weight, for example having a net weight (without liquid) of 5 gms or less, preferably 3 gms or less, and have a connector adapted to attach to the weaker smaller diameter tube 6. Such "miniature" nebulizers may have a small reservoir that holds one unit dose of medicament, e.g. less than 4 ml of liquid, and a light-weight aerosol generator, e.g. on the order of about 1 gm in weight. In addition, preferred nebulizers are quiet in operation, e.g. producing less than 5 decibels of sound pressure, so that they can conveniently be placed very close to the patient.

The flow sensor 9 of the present invention may be a known flow sensor device that is adapted to detect small changes in the volumetric flow rate of fluid passing through it and is capable of generating an electronic signal, e.g. an output voltage, that is characteristic of that flow rate. A particularly preferred flow sensor for the practice of the present invention is commercially available from Omron Corporation of Japan, and is identified as "MEMS Flow Sensor, Model D6F-01A1-110". The Omron flow sensor is capable of detecting a flow rate in the range of 0 to 1 L/min (at 0° C. and 101.3 kPa pressure). The relationship of measured flow rate and resulting output voltage for the Omron flow sensor is summarized in Table 1 below:

TABLE 1

| | Flow rate (L/min) | | | | | |
|---|---|---|---|---|---|---|
| | 0 | 0.2 | 0.4 | 0.6 | 0.8 | 1.0 |
| Output voltage (VDC ± 0.12) | 1.00 | 2.31 | 3.21 | 3.93 | 4.51 | 5.00 |

[Note: measurement conditions for Table 1 are as follows: power-supply voltage of 12 VDC, ambient temperature of 25° C. and ambient humidity of 25-75% RH.]

Nebulizer apparatus 7 may be connected to flow sensor 9 through the electronic circuitry 25 of the CPAP system. For example, nebulizer 7 may be connected to a controller (not shown) that turns the aerosol generator off and on in response to signals from flow sensor 9. Preferably, the controller and other electronic components of the CPAP system are connected with wires, cables and connectors that are small and flexible. Examples of other components that may also be associated with nebulizer apparatus 7 are a timer, status indication means, liquid medicament supply nebule or syringe, etc., all as known by those skilled in the art and described in detail in the aforementioned patent and patent applications.

The following examples will illustrate the present invention using the Omron flow sensor described above, but is not intended to limit the invention to the particular details set forth therein:

EXAMPLE 1

A CPAP system of the present invention such as illustrated in FIGS. 1 and 2 may be used for respiratory treatment of an infant. The system may be pressurized to a pressure of 5 cm $H_2O$ and a constant flow of air may be supplied by flow generator 2 into pressure-generating circuit P at a rate of 10 L/min. About 1 L/min (10%) of the air flow in pressure-generating circuit P may flow into flexible tube 6 as flow 21. During inhalation by the infant through nasal cannula 4, about 20% of flow 21 (identified in FIG. 2 as flow 21*b*) may be diverted into tube 11 at junction 10 by appropriately adjusting orifice valve 12 to produce a flow rate for flow 21*c* of about 0.2 L/min (0.2×1 L/min). Flow 21*c* may also pass through a disposable filter 13, but since flow 21*c* contains only inhalation air containing very little, if any, contamination, nothing significant should be removed from flow 21*c* by the filter. Flow 21*c* then may pass through the Omron flow sensor described above at a flow rate of 0.2 L/min, which according to Table 1 above, results in the generation of an output voltage of about 2.31 VDC. The electronic circuitry of the CPAP system may be configured to have the aerosol generator of nebulizer 7 turned on when the flow sensor is transmitting this output voltage to nebulizer 7. Turning on the aerosol generator introduces aerosolized medicament into the respiratory circuit R of the CPAP system so it can be inhaled by the infant.

During exhalation, the infant may exhale about 0.6 L/min of air flow through nasal cannula 4 to produce expiratory flow 24, which combines in tube 11 with flow 21*b*. As previously described for flow 21*b* alone, orifice valve 12 has been adjusted to reduce the flow rate of gas in tube 6 to about 20% of the original flow rate. Accordingly, flow 21*b* may be reduced to flow 21*c* having a flow rate of about 0.20 L/min (0.2×1 L/min) and flow 24 may be reduced to flow 24*a* having a flow rate of about 0.12 L/min (0.2×0.6 L/min). The combined expiratory flow rate of the combination of flow 21*c* and 24*a* therefore equals about 0.32 L/min. This combined expiratory flow rate may then pass through disposable filter 13 to remove any contaminates that may be present as a result of expiratory flow 24*a*, and then pass through the Omron flow sensor. Again referring to Table 1 above, it can be seen that the Omron pressure sensor generates an output voltage of about 3.0 VDC at the combined exhalation flow rate of 0.32 L/min. The electronic circuitry of the CPAP system may be configured to have the aerosol generator of nebulizer 7 turned off when this output voltage is transmitted to nebulizer 7 by electronic circuitry 25. Turning off the aerosol generator ceases the introduction of aerosolized medicament particles 22 into the respiratory circuit R of the CPAP system during the presence of expiratory flow 24. As a result, a minimum amount of aerosol is entrained in expiratory flow 24 and ultimately lost to the atmosphere. In some cases, electronic circuitry 25 may include a phase shift circuit which can slightly advance or delay the inactivation of the aerosol generator, if desired.

When the flow rate through the Omron flow sensor returns to 0.2 L/min during inhalation, the output voltage of the Omron flow sensor returns to 2.31 VDC. Since this voltage is characteristic of the inhalation phase of the patient's respiratory cycle, it may be used by electronic circuitry 25 as a signal to turn on the aerosol generator again so that the introduction of aerosolized medicament into the respiratory circuit of the CPAP system is resumed during inhalation. The cycle of turning the nebulizer on and off depending on what phase of the patient's respiratory cycle is occurring may be repeated during the period that the CPAP system is used for respiratory treatment of the infant, thereby significantly reducing the amount of medicament needed for such treatment.

EXAMPLE 2

Figure 3:
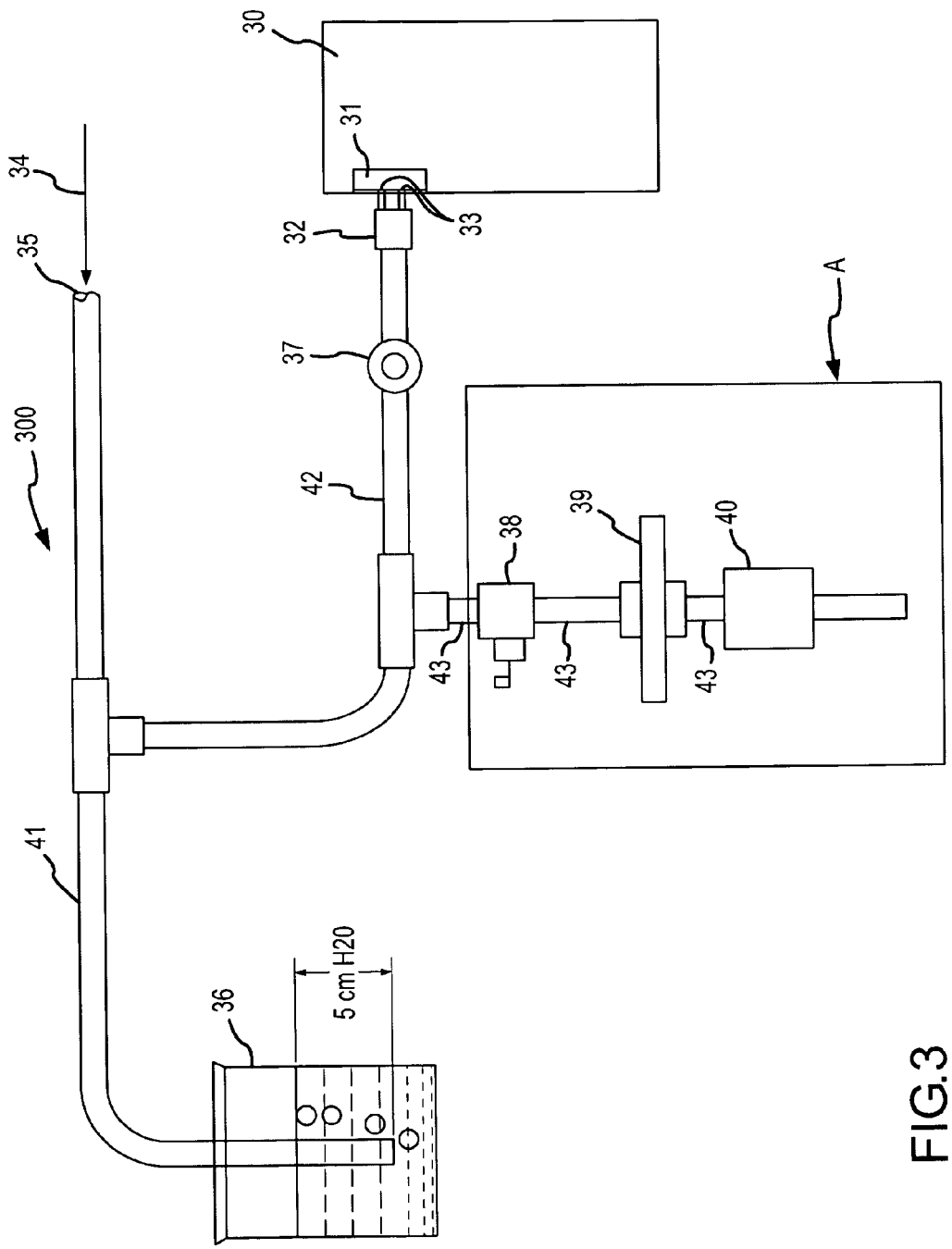
FIG. 3 is a schematic illustration of a CPAP system described in Example 2.

Referring to FIG. 3, CPAP system 300 was attached to a breathing simulation piston pump 30 (commercially available from Harvard Apparatus, Holliston, Mass. 01746) to simulate an infant's breathing cycle. CPAP system 300 included auxiliary circuit A comprising pressure valve 38, disposable filter 39 and flow sensor 40 connected to respiratory circuit 42 through tube 43 in accordance with the present invention. A removable filter 31 was placed at the inlet of pump 30. An adapter 32 with two orifices 33 representing infant nares (Argyle nasal prong commercially available from Sherwood Medical, St. Louis, Mo. 63013) was connected to filter 31. Nebulizer 37 (Aeroneb® Professional Nebulizer System commercially available from Aerogen, Inc., Mountain View, Calif.) was placed in respiratory circuit 42 near adapter 32 so as to deliver an aerosolized drug into the air flow passing through orifices 33. During the operation of pump 30, air containing the entrained aerosolized drug flowed back and forth through filter 31, which collected the drug from the air flow. The amount of drug collected on filter 31 after each test was measured by high-pressure liquid chromatography (HPLC) and compared to the total amount that was nebulized to provide a measure of the efficiency of aerosol delivery to the system.

Pump 30 was set to infant ventilatory parameters with a tidal volume of 10 ml and a respiratory rate of 40 breaths per minute. A constant air flow 34 of 10 L/min was provided through CPAP inlet 35 and resistance pressure regulator 36 was set to generate a pressure of 5 cm $H_2O$. Nebulizer 37 was filled with 3 ml of a solution of albuterol sulfate ("albuterol"). In order to study the effect of synchronized nebulization (i.e., nebulization during inhalation only) versus continuous nebulization, two separate sets of 4 tests were conducted. In the first set of tests, nebulizer 37 ran continuously during both the inhalation and exhalation cycles of pump 30. In the second set of tests, the operation of nebulizer 37 was stopped during the exhalation cycle of pump 30 using the input from flow sensor 40 in accordance with the present invention. After each test, the amount of albuterol collected on filter 31 was measured by HPLC and compared with the amount of albuterol nebulized to obtain a percent efficiency. The results are summarized in Table 2 below:

TABLE 2

| Test No. | Efficiency |
|---|---|
| Continuous Nebulization: | |
| 1 | 26% |
| 2 | 24% |
| 3 | 22% |
| 4 | 27% |
| Average Efficiency: | 24.75% |
| Synchronized Nebulization: | |
| 1 | 40% |
| 2 | 44% |

TABLE 2-continued

| Test No. | Efficiency |
|---|---|
| 3 | 51% |
| 4 | 43% |
| Average Efficiency: | 44.5% |

The above results demonstrate that synchronized nebulization according to the present invention may deliver an order of magnitude more albuterol through nasal prongs during CPAP than continuous nebulization.

The high efficiency of delivery of aerosolized medicaments according to the present invention is particularly valuable in respiratory therapies that utilize expensive or scarce medicaments, such as the aforementioned NCPAP treatment of iRDS using aerosolized surfactants. Since most surfactants are animal-based, the current supply is limited, and although synthetic surfactants are available, their manufacture is both inexact and expensive. In addition, the surfactant medicaments are typically high in viscosity and are difficult to deliver to the patient's respiratory system. The increased efficiency of the pressure-assisted breathing system of the present invention, and the smaller amount of medicament required for a treatment according to the present invention, can be a substantial advantage when such scarce and expensive medicaments are employed.

It is understood that while the invention has been described above in connection with preferred specific embodiments, the description and drawings are intended to illustrate and not limit the scope of the invention, which is defined by the appended claims and their equivalents.

What is claimed is:

1. A CPAP apparatus for the delivery of an aerosolized medicament to a patient's respiratory system comprising:
   a pressure-generating circuit that maintains continuous positive pressure throughout the apparatus during the breathing cycle of the patient;
   a patient interface device adapted to be coupled to a patient's respiratory system;
   a respiratory circuit that provides gas communication between the pressure-generating circuit and the patient interface device, whereby the patient breathes gas under continuous positive pressure;
   a nebulizer that introduces aerosolized medicament into the gas flow in the respiratory circuit;
   an auxiliary circuit in gas communication with the respiratory circuit whereby a portion of the gas flow in the respiratory circuit is diverted to the external atmosphere to provide a secondary gas flow;
   a flow sensor disposed in the auxiliary circuit for measuring the flow rate of the secondary gas flow; and
   electronic circuitry connecting the flow sensor to the nebulizer, whereby the flow sensor sends a first electronic signal that causes the nebulizer to turn off when the flow sensor detects an increase in the flow rate of the secondary gas flow as the result of the patient commencing exhalation.

2. Apparatus according to claim 1 wherein the flow sensor sends a second signal that causes the nebulizer to turn on when the flow sensor detects a decrease in the flow rate of the secondary gas flow as the result of the patient ceasing exhalation.

3. Apparatus according to claim 2 wherein each signal is a certain output voltage generated by the flow sensor.

4. Apparatus according to claim 1 wherein the flow sensor is adapted to measure a range of flow rates less than the flow rate of the secondary gas flow; and further comprising a valve disposed in the auxiliary circuit for reducing the flow rate of the secondary gas flow to the measurement range of the flow sensor.

5. Apparatus according to claim 4 wherein the flow sensor has a flow range of 0 to 1 L/min and the valve regulates the flow of gas to about the middle of said range.

6. Apparatus according to claim 1 further comprising a disposable filter for trapping contaminants prior to passing through the flow sensor.

7. Apparatus according to claim 1 wherein the nebulizer comprises a reservoir for holding a liquid medicament to be delivered to the patient's respiratory system, a vibrating aperture-type aerosol generator for aerosolizing the liquid medicament and a connector for connecting the nebulizer to the respiratory circuit so as to entrain the aerosolized medicament from the aerosol generator into the gas flowing through the respiratory circuit.

8. Apparatus according to claim 7 wherein said liquid medicament is a surfactant.

9. A method of delivering an aerosol to a patient's respiratory system which comprises the steps of:
   providing a CPAP system having a pressure-generating circuit that provides continuous positive pressure throughout the apparatus during the breathing cycle of the patient, a respiratory circuit coupled to a patient interface device whereby the patient breathes gas under continuous positive pressure and an auxiliary circuit in gas communication with the respiratory circuit that diverts a portion of the gas flow in the respiratory circuit to the external atmosphere to provide a secondary gas flow, the auxiliary circuit having disposed therein a flow sensor electronic ally connected to a nebulizer coupled to the respiratory circuit;
   introducing a liquid into the nebulizer;
   regulating the flow rate of the secondary gas flow to a range that can be measured by the flow sensor; and
   turning on the nebulizer to introduce an aerosol of the liquid into the respiratory circuit, or turning off the nebulizer to cease introduction of aerosol into the respiratory circuit, in response to at least one change in the flow rate of secondary gas flow that the flow sensor detects in the auxiliary circuit.

10. A pressure-assisted breathing system comprising:
    a pressure-generating circuit for maintaining a positive pressure throughout the apparatus during the breathing cycle of a patient;
    a patient interface device adapted to be coupled to the patient's respiratory system;
    a respiratory circuit for providing gas communication between the pressure-generating circuit and the patient interface device, whereby the patient breathes gas under continuous positive pressure;
    an auxiliary circuit in fluid communication with the respiratory circuit that diverts a portion of the reduced gas flow in the respiratory circuit to the external atmosphere to provide a secondary gas flow;
    means for introducing aerosol particles into the gas flow in the respiratory circuit;
    a flow sensor disposed in the auxiliary circuit that is adapted to measure gas flow rates less than the flow rate of the secondary gas flow, wherein the flow sensor is electronically coupled with the means for introducing the aerosol particles into the respiratory circuit gas flow; and
    a valve disposed in the auxiliary circuit for reducing the secondary gas flow to a flow rate that can be measured by the flow sensor;
    wherein said flow sensor is adapted to detect a change in the flow rate of the secondary gas flow when the patient exhales and inhales, and thereby send a corresponding electronic signal tat causes the means for introducing aerosol particles to turn off during exhalation and turn on during inhalation.

11. A system according to claim 10 wherein the auxiliary circuit further comprises a disposable filter for trapping contaminants in the flow of gas before it passes through the flow sensor.

12. A system according to claim 10 wherein the means for introducing aerosol particles comprises a nebulizer.

13. A system according to claim 12 wherein the nebulizer comprises a reservoir for holding a liquid medicament to be delivered to the patient's respiratory system, a vibrating aperture-type aerosol generator for aerosolizing the liquid medicament and a connector for connecting the nebulizer to the respiratory circuit so as to entrain the aerosolized medicament from the aerosol generator into the gas flowing through the respiratory circuit.

* * * * *